US010086061B2

(12) United States Patent
Thomas et al.

(10) Patent No.: US 10,086,061 B2
(45) Date of Patent: Oct. 2, 2018

(54) COMBINATION PURIFIED INACTIVATED VACCINE FOR FLAVIVIRUSES

(71) Applicant: The United States of America, as represented by the Secretary of the Army, on behalf of the Walter Reed Army Institute of Research, Washington, DC (US)

(72) Inventors: Stephen J. Thomas, Rockville, MD (US); Kenneth H. Eckels, Rockville, MD (US); Joseph R. Putnak, Silver Spring, MD (US)

(73) Assignee: The United States of America, as represented by the Secretary of the Army, on behalf of the Walter Reed Army Institute of Research, Washington, DC (US)

( * ) Notice: Subject to any disclaimer, the term of this patent is extended or adjusted under 35 U.S.C. 154(b) by 0 days.

(21) Appl. No.: 15/550,433

(22) PCT Filed: Mar. 10, 2016

(86) PCT No.: PCT/US2016/021696
§ 371 (c)(1),
(2) Date: Aug. 11, 2017

(87) PCT Pub. No.: WO2016/145149
PCT Pub. Date: Sep. 15, 2016

(65) Prior Publication Data
US 2018/0021426 A1 Jan. 25, 2018

Related U.S. Application Data

(60) Provisional application No. 62/131,326, filed on Mar. 11, 2015.

(51) Int. Cl.
*A61K 39/12* (2006.01)
*A61K 39/395* (2006.01)
*A61K 39/00* (2006.01)
*C12N 7/00* (2006.01)

(52) U.S. Cl.
CPC ............ *A61K 39/12* (2013.01); *A61K 39/395* (2013.01); *A61K 2039/5252* (2013.01); *A61K 2039/545* (2013.01); *A61K 2039/70* (2013.01); *C12N 7/00* (2013.01); *C12N 2770/24034* (2013.01); *C12N 2770/24051* (2013.01); *C12N 2770/24134* (2013.01); *C12N 2770/24151* (2013.01); *Y02A 50/386* (2018.01); *Y02A 50/388* (2018.01); *Y02A 50/39* (2018.01); *Y02A 50/392* (2018.01); *Y02A 50/394* (2018.01)

(58) Field of Classification Search
CPC .. A61K 2300/00; A61K 39/12; A61K 9/0019; A61K 2039/5254; A61K 2039/70; A61K 39/395; A61K 2039/545; A61K 2039/5252; C12N 7/00; C12N 2770/24134; C12N 2770/24051; C12N 2770/24151; C12N 2770/24034; C07K 14/005; C07K 14/1825; Y02A 50/394; Y02A 50/388; Y02A 50/392; Y02A 50/386; Y02A 50/39

See application file for complete search history.

(56) References Cited

U.S. PATENT DOCUMENTS

| 6,190,859 B1 * | 2/2001 | Putnak | C12N 7/00 424/184.1 |
| 6,254,873 B1 * | 7/2001 | Putnak | A61K 39/12 424/202.1 |
| 2013/0295162 A1 | 11/2013 | Schlesinger et al. | |
| 2017/0035875 A1 * | 2/2017 | Simmons | A61K 39/12 |
| 2018/0021426 A1 * | 1/2018 | Thomas | A61K 39/12 |

FOREIGN PATENT DOCUMENTS

WO WO-2012160199 A1 * 11/2012 ............. A61K 39/12

OTHER PUBLICATIONS

Fernandez S, et. al. An adjuvanted, tetravalent dengue virus purified inactivated vaccine candidate induces long-lasting and protective antibody responses against dengue challenge in rhesus macaques. Am J Trop Med Hyg. Apr. 2015;92(4):698-708. Epub Feb. 2, 2015.*
Thisyakorn U, Thisyakorn C. Latest developments and future directions in dengue vaccines. Ther Adv Vaccines. Jan. 2014;2(1):3-9.*
Weaver SC, Reisen WK. Present and future arboviral threats. Antiviral Res. Feb. 2010;85(2):328-45. Epub Oct. 24, 2009.*
Imoto, et al., "Dengue tetravalent DNA vaccine increases its immunogenicity in mice when mixed with a dengue type 2 subunit vaccine or an inactivated Japanese encephalitis vaccine", Dec. 20, 2006, pp. 1076-1084, vol. 25, No. 6, Publisher: Vaccine.
International Search Report received in PCT/US2016/021696, dated Jun. 2, 2016.
Written Opinion received in PCT/US2016/021696, dated Jun. 2, 2016.
Anderson, et al., "Interference and Facilitation between Dengue Stereotypes in the Tetravalent Live Dengue Virus Vaccine Candidate", Aug. 1, 2011, p. 442-450, vol. 204, Publisher: JID.
Melendrez, Mel, "Blog Article entitled: NIAID-DVI: GSK/FIOCRUZ/US Tetravalent DPIV—Alexander Schmidt", Sep. 9, 2013, Publisher: http://weallseqtoseq.blogspot.com/2013/09/niaid-dvi-gskfiocruzus-tetravalent-dpiv.html.
GSK Biologicals, "Tetravalent Dengue Purified Inactivated Vaccine (DPIV)", Apr. 17, 2013, PowerPoint Presentation.

(Continued)

*Primary Examiner* — Rachel B Gill
(74) *Attorney, Agent, or Firm* — Elizabeth Arwine, Esq.

(57) ABSTRACT

Immunogenic compositions comprising one or more inactivated dengue viruses and one or more inactivated non-dengue flaviviruses and methods of making and using thereof are provided.

20 Claims, No Drawings

(56) References Cited

OTHER PUBLICATIONS

Guirakhoo, et al., "Immunogenicity, Genetic Stability, and Protective Efficacy of a Recombinant, Chimeric Yellow Fever-Japanese Encephalitis Virus (ChimeriVax-JE) as . . . ", Mar. 10, 1999, pp. 363-372, vol. 257, Publisher: Virology.

Guirakhoo, et al., "Viremia and Immunogenicity in Nonhuman Primates of a Tetravalent Yellow FeverDengue Chimeric Vaccine: Genetic Reconstructions, Dose Adjustment, . . . ", Mar. 12, 2002, pp. 146-159, No. 298, Publisher: Virology.

Halstead, SB, "Safety Issues from a Phase 3 Clinical Trial of a Live-Attenuated Chimeric Yellow Fever Tetravalent Dengue Vaccine", Feb. 26, 2018, Page(s) Abstract, Publisher: Hum Vaccin Immunother.

Halstead and Thomas, "Chapter 44—Dengue Vaccines", Nov. 7, 2012, Page(s) https://doi.org/10.1016/8978-1-4557-0090-5.00047-1, Publisher: Vaccines (Sixth Ed.) Elsevier.

Monath, et al., "Inactivated yellow fever 17D vaccine: development and nonclinical safety,, immunogenicity and protective activity", Mar. 26, 2010, Page(s) Abstract, vol. 28, No. 22, Publisher: Vaccine.

"NCT01666652", Aug. 15, 2012, Publisher: ClinicalTrials.gov.

Ortega-Barria, Eduardo, "Rationale for and Status of GSK/FIOCRUZ/WRAIR New Dengue Vaccine Candidate", Sep. 21, 2011, PowerPoint Presentation.

Sabchareon, et al., "Safety and immunogenicity of tetravalent live-attenuated dengue vaccines in Thai adult volunteers: role of serotype concentration, ratio, and mult . . . ", Mar. 1, 2002, pp. 264-272, vol. 66, No. 6, Publisher: Am. J. Trop. Med. Hyg.

Simmons, et al., "Protection against Dengue Virus by Non-Replicating and Live Attenuated Vaccines Used Together in a Prime Boost Vaccination Strategy", Nov. 13, 2009, pp. 280-288, vol. 396, Publisher: Virology.

Thomas, et al., "Critical Issues in Dengue Vaccine Development", Oct. 1, 2011, pp. 442-450, vol. 24, Publisher: Curr Opin Infect Dis.

Thomas, et al., "Current Issues in Dengue Vaccination", Oct. 1, 2013, pp. 429-434, vol. 26, No. 5, Publisher: Curr Opin Infect Dis.

Yao, et al., "Study on a purified and inactivated Japanese encephalitis vaccine prepared on Vero cells using SA14-14-2 attenuated virus strain", Jun. 30, 1999, Page(s) Abstract, vol. 13, No. 2, Publisher: Zhonghua Shi Yan He Lin Chuang Bing Du Xue Za Zhi.

* cited by examiner

COMBINATION PURIFIED INACTIVATED VACCINE FOR FLAVIVIRUSES

ACKNOWLEDGEMENT OF GOVERNMENT SUPPORT

This invention was made by employees of the United States Army Medical Research and Materiel Command, which is an agency of the United States Government. The Government has certain rights in the invention.

BACKGROUND OF THE INVENTION

1. Field of the Invention

The present invention relates to immunogenic compositions which comprise at least one inactivated dengue virus and at least one inactivated non-dengue flavivirus, and methods of making and using thereof.

2. Description of the Related Art

Flaviviruses are enveloped, single-stranded, positive-sense RNA viruses in the genus Flavivirus, family Flaviviridae. The viral RNA genome is approximately 11 kb in length and contains one long open reading frame (ORF) encoding four virion structural proteins, capsid (C), membrane (M), its precursor pre-membrane (prM), and envelope (E), and 7 non-structural (NS) proteins, NS1, NS2A, NS2B, NS3, NS4A, NS4B, and NS5, flanked by 5'- and 3'-untranslated regions (5'UTR/3'UTR), approximately 100 and 450 nucleotides (nt) long, respectively. All viral proteins derive from the post-translational processing of a polyprotein precursor by both virally-encoded and host proteinases. The C protein comprises the virion core, which encapsidates the viral RNA genome. The prM, M, and E proteins are integral membrane proteins within the virion envelope. In completely matured, infectious virions the E protein exists as an N-glycosylated dimer, 180 copies per virion, along with an equal number of M protein molecules. The NS proteins, although they are not incorporated into the virion, play critical roles in the virus life cycle, including proteolytic processing, RNA replication, virion maturation, and the modulation of host cell functions and activities such as those involved in interferon and apoptosis pathways.

There are nearly 70 known flaviviruses, 30 of which have been associated with human diseases of varying incidence and severity. The flaviviruses were originally grouped and typed by their reactivity in serological assays (i.e., virus-neutralization, hemagglutination, and complement-fixation) according to their unique (virus specific) or shared (cross-reactive) antigenic determinants. These groupings were later confirmed and extended by monoclonal antibody mapping of discrete epitopic determinants and genetic sequence analysis of the viral RNAs. Arguably, the most medically important flaviviruses in terms of disease incidence and severity are the arthropod-borne viruses or Arboviruses, particularly those in Group B, which are transmitted by mosquito or tick vectors. These include the dengue virus (DENV), yellow fever virus (YFV), Japanese encephalitis virus (JEV), and West Nile virus (WNV), Zika virus (ZIKV), St. Louis encephalitis virus (SLEV), Tick-borne encephalitis virus (TBEV) (including the Russian Spring Summer encephalitis virus (RSSEV)).

The disease burden from flavivirus infections is enormous and growing, especially considering that accurate estimates of incidence are hampered by asymptomatic disease, under-reporting, and limited diagnostic capabilities in many endemic areas. For example, current estimates suggest that more than 3.6 billion people may be at risk for infection by DENV in the tropics and subtropics in both the eastern and western hemispheres where the primary mosquito vector *Aedes aegypti* is prevalent. It is estimated nearly 400 million infections by DENV occur each year with over 95 million being symptomatic and 2 million severe.

Individuals, including United States military personnel, are at significant risk for infection by flaviviruses, such as YFV, JEV, DENV, and ZIKV when stationed or travelling in endemic areas and those living in North America are at risk of infection by WNV. The Southern United States has mosquito vectors capable of transmitting flaviviruses as evidence by the annual occurrence of DENV transmission in Florida and Texas. There are existing licensed (U.S. and foreign) live attenuated YFV and inactivated JEV and Tick-Borne Encephalitis (TBE) vaccines and live attenuated chimeric vaccines based on ChimeriVax® technology against JEV, DENV, and WNV. There has yet to be developed a vaccine for ZIKV. Most inactivated and attenuated flavivirus vaccines against a given flavivirus require a burdensome 2 to 3 dose primary immunization regimen which requires completion about one month prior to exposure to the flavivirus. In the case of DENV ChimeriVax®, the immunization schedule spans one year (dosing 0, 6, and 12 months). The inactivated JEV vaccine (IXIARO®) requires at least 2 doses for protective immunization.

Although some flaviviruses are restricted to specific regions of the world, many are more widespread and there are significant overlaps. For example, in Africa and the Americas both DENV and YFV are present, whereas in larger parts of Asia, DENV and JEV are endemic. ZIKV is now actively transmitted in Asia, Africa, and the Americas. Thus, before traveling to places like Africa and Asia, one must undergo lengthy, multiple immunizations regimens.

Therefore, a need exists for a single vaccine composition that effectively protects against multiple, different flaviviruses.

SUMMARY OF THE INVENTION

The present invention provides immunogenic compositions comprising one or more inactivated dengue viruses and one or more inactivated non-dengue flaviviruses and a pharmaceutically acceptable vehicle. The present invention provides immunogenic compositions consisting essentially of one or more inactivated dengue viruses and one or more inactivated non-dengue flaviviruses and a pharmaceutically acceptable vehicle. The present invention provides immunogenic compositions consisting of one or more inactivated dengue viruses and one or more inactivated non-dengue flaviviruses and a pharmaceutically acceptable vehicle. In some embodiments, the one or more inactivated dengue viruses and the one or more inactivated non-dengue flaviviruses are each provided in an immunogenically effective amount. In some embodiments, some or all of the inactivated viruses are purified. In some embodiments, the one or more inactivated dengue viruses are selected from the group consisting of an inactivated DENV-1, an inactivated DENV-2, an inactivated DENV-3, and an inactivated DENV-4. In some embodiments, the one or more inactivated dengue viruses consist of an inactivated DENV-1, an inactivated DENV-2, an inactivated DENV-3, and an inactivated DENV-4. In some embodiments, the one or more inactivated dengue viruses comprise or consist of 1, 2, 3, or 4 DENV serotypes. In some embodiments, the dengue virus is an inactivated DENV-1 produced from deposited DENV-1 strain having ATCC accession number VR-2649. In some embodiments, the dengue virus is an inactivated DENV-2 produced from deposited DENV-2 strain having ATCC accession number VR-2650. In some embodiments, the dengue virus is an inactivated DENV-3 produced from deposited DENV-3 strain having ATCC accession number VR-2654. In some embodiments, the dengue virus is an inactivated DENV-4 produced from deposited DENV-4 strain having ATCC accession number VR-2651. In some embodiments, the one or more inactivated non-dengue flaviviruses are selected from the group consisting of yellow fever group viruses and Japanese encephalitis group viruses. In some embodiments, the one or more inactivated non-dengue flaviviruses are selected from the group consisting of yellow fever virus (YFV), Japanese encephalitis virus (JEV), and West Nile virus (WNV). In some embodiments, the one or more inactivated non-dengue flaviviruses are yellow fever virus (YFV) and Japanese encephalitis virus (JEV). In some embodiments, the one or more inactivated non-dengue flavivirus includes Zika virus (ZIKV). In some embodiments, the one or more inactivated non-dengue flavivirus is Zika virus (ZIKV). In some embodiments, the one or more inactivated dengue viruses are present in an immunologically effective amount and/or the one or more inactivated non-dengue flaviviruses are present in an immunologically effective amount. In some embodiments, each of the one or more inactivated dengue viruses are present in an immunologically effective amount. In some embodiments, the one or more inactivated dengue viruses are purified and/or the one or more inactivated non-dengue flaviviruses are purified. In some embodiments, the immunogenic composition further comprises an adjuvant. In some embodiments, the immunogenic composition is a mixture of one or more inactivated DENV and XRX-001 Yellow Fever 17D inactivated vaccine (GE Healthcare). In some embodiments, the immunogenic composition is a mixture of one or more inactivated DENV and IXIARO® vaccine (Intercell USA, Inc.). In some embodiments, the immunogenic composition is a mixture of one or more inactivated DENV, XRX-001 Yellow Fever 17D inactivated vaccine (GE Healthcare), and IXIARO® vaccine (Intercell USA, Inc.).

In some embodiments, the present invention provides methods of producing antibodies against a dengue virus and a non-dengue flavivirus in a subject, which comprises administering to the subject an immunogenic composition comprising, consisting essentially of, or consisting of one or more inactivated dengue viruses and one or more inactivated non-dengue flaviviruses and a pharmaceutically acceptable vehicle. In some embodiments, the one or more inactivated dengue viruses and the one or more inactivated non-dengue flaviviruses are each provided in an immunogenically effective amount. In some embodiments, some or all of the inactivated viruses are purified. In some embodiments, the one or more inactivated dengue viruses are selected from the group consisting of an inactivated DENV-1, an inactivated DENV-2, an inactivated DENV-3, and an inactivated DENV-4. In some embodiments, the one or more inactivated dengue viruses consist of an inactivated DENV-1, an inactivated DENV-2, an inactivated DENV-3, and an inactivated DENV-4. In some embodiments, the one or more inactivated dengue viruses comprise or consist of 1, 2, 3, or 4 DENV serotypes. In some embodiments, the dengue virus is an inactivated DENV-1 produced from deposited DENV-1 strain having ATCC accession number VR-2649. In some embodiments, the dengue virus is an inactivated DENV-2 produced from deposited DENV-2 strain having ATCC accession number VR-2650. In some embodiments, the dengue virus is an inactivated DENV-3 produced from deposited DENV-3 strain having ATCC accession number VR-2654. In some embodiments, the dengue virus is an inactivated DENV-4 produced from deposited DENV-4 strain having ATCC accession number VR-2651. In some embodiments, the one or more inactivated non-dengue flaviviruses are selected from the group consisting of yellow fever group viruses and Japanese encephalitis group viruses. In some embodiments, the one or more inactivated non-dengue flaviviruses are selected from the group consisting of yellow fever virus (YFV), Japanese encephalitis virus (JEV), and West Nile virus (WNV). In some embodiments, the one or more inactivated non-dengue flaviviruses are yellow fever virus (YFV) and Japanese encephalitis virus (JEV). In some embodiments, the one or more inactivated non-dengue flavivirus includes Zika virus (ZIKV). In some embodiments, the one or more inactivated non-dengue flavivirus is Zika virus (ZIKV). In some embodiments, the one or more inactivated dengue viruses are present in an immunologically effective amount and/or the one or more inactivated non-dengue flaviviruses are present in an immunologically effective amount. In some embodiments, each of the one or more inactivated dengue viruses are present in an immunologically effective amount. In some embodiments, the one or more inactivated dengue viruses are purified and/or the one or more inactivated non-dengue flaviviruses are purified. In some embodiments, the immunogenic composition further comprises an adjuvant. In some embodiments, the immunogenic composition is a mixture of one or more inactivated DENV and XRX-001 Yellow Fever 17D inactivated vaccine (GE Healthcare). In some embodiments, the immunogenic composition is a mixture of one or more inactivated DENV and IXIARO® vaccine (Intercell USA, Inc.). In some embodiments, the immunogenic composition is a mixture of one or more inactivated DENV, XRX-001 Yellow Fever 17D inactivated vaccine (GE Healthcare), and IXIARO® vaccine (Intercell USA, Inc.). In some embodiments, the immunogenic composition is administered as a single dose on a 0-28 day vaccination schedule. In some embodiments, the immunogenic composition is administered by intramuscular injection. In some embodiments, the subject is a non-human animal, such as rodents and non-human primates, which may or may not be laboratory test animals. In some embodiments, the subject is a human. In some embodiments, the subject is at risk of being exposed to one or more flaviviruses.

In some embodiments, the present invention provides medicaments for producing antibodies against a dengue virus and a non-dengue flavivirus in a subject, which comprises an immunogenic composition comprising, consisting essentially of, or consisting of one or more inactivated dengue viruses and one or more inactivated non-dengue flaviviruses and a pharmaceutically acceptable vehicle. In some embodiments, the one or more inactivated dengue viruses and the one or more inactivated non-dengue flaviviruses are each provided in an immunogenically effective amount. In some embodiments, some or all of the inactivated viruses are purified. In some embodiments, the one or more inactivated dengue viruses are selected from the group consisting of an inactivated DENV-1, an inactivated DENV-2, an inactivated DENV-3, and an inactivated DENV-4. In some embodiments, the one or more inactivated dengue viruses consist of an inactivated DENV-1, an inactivated DENV-2, an inactivated DENV-3, and an inactivated DENV-4. In some embodiments, the one or more inactivated dengue viruses comprise or consist of 1, 2, 3, or 4 DENV serotypes. In some embodiments, the dengue virus is an inactivated DENV-1 produced from deposited DENV-1 strain having ATCC accession number VR-2649. In some embodiments, the dengue virus is an inactivated DENV-2 produced from deposited DENV-2 strain having ATCC accession number VR-2650. In some embodiments, the dengue virus is an inactivated DENV-3 produced from deposited DENV-3 strain having ATCC accession number VR-2654. In some embodiments, the dengue virus is an inactivated DENV-4 produced from deposited DENV-4 strain having ATCC accession number VR-2651. In some embodiments, the one or more inactivated non-dengue flaviviruses are selected from the group consisting of yellow fever group viruses and Japanese encephalitis group viruses. In some embodiments, the one or more inactivated non-dengue flaviviruses are selected from the group consisting of yellow fever virus (YFV), Japanese encephalitis virus (JEV), and West Nile virus (WNV). In some embodiments, the one or more inactivated non-dengue flaviviruses are yellow fever virus (YFV) and Japanese encephalitis virus (JEV). In some embodiments, the one or more inactivated non-dengue flavivirus includes Zika virus (ZIKV). In some embodiments, the one or more inactivated non-dengue flavivirus is Zika virus (ZIKV). In some embodiments, the one or more inactivated dengue viruses are present in an immunologically effective amount and/or the one or more inactivated non-dengue flaviviruses are present in an immunologically effective amount. In some embodiments, each of the one or more inactivated dengue viruses are present in an immunologically effective amount. In some embodiments, the one or more inactivated dengue viruses are purified and/or the one or more inactivated non-dengue flaviviruses are purified. In some embodiments, the immunogenic composition further comprises an adjuvant. In some embodiments, the immunogenic composition is a mixture of one or more inactivated DENV and XRX-001 Yellow Fever 17D inactivated vaccine (GE Healthcare). In some embodiments, the immunogenic composition is a mixture of one or more inactivated DENV and IXIARO® vaccine (Intercell USA, Inc.). In some embodiments, the immunogenic composition is a mixture of one or more inactivated DENV, XRX-001 Yellow Fever 17D inactivated vaccine (GE Healthcare), and IXIARO® vaccine (Intercell USA, Inc.). In some embodiments, the subject is a non-human animal, such as rodents and non-human primates, which may or may not be laboratory test animals. In some embodiments, the subject is a human. In some embodiments, the subject is at risk of being exposed to one or more flaviviruses.

In some embodiments, the present invention is directed to the use of an immunogenic composition comprising, consisting essentially of, or consisting of one or more inactivated dengue viruses and one or more inactivated non-dengue flaviviruses and a pharmaceutically acceptable vehicle. In some embodiments, the one or more inactivated dengue viruses and the one or more inactivated non-dengue flaviviruses are each provided in an immunogenically effective amount. In some embodiments, some or all of the inactivated viruses are purified. In some embodiments, the one or more inactivated dengue viruses are selected from the group consisting of an inactivated DENV-1, an inactivated DENV-2, an inactivated DENV-3, and an inactivated DENV-4. In some embodiments, the one or more inactivated dengue viruses consist of an inactivated DENV-1, an inactivated DENV-2, an inactivated DENV-3, and an inactivated DENV-4. In some embodiments, the one or more inactivated dengue viruses comprise or consist of 1, 2, 3, or 4 DENV serotypes. In some embodiments, the dengue virus is an inactivated DENV-1 produced from deposited DENV-1 strain having ATCC accession number VR-2649. In some embodiments, the dengue virus is an inactivated DENV-2 produced from deposited DENV-2 strain having ATCC accession number VR-2650. In some embodiments, the dengue virus is an inactivated DENV-3 produced from deposited DENV-3 strain having ATCC accession number VR-2654. In some embodiments, the dengue virus is an inactivated DENV-4 produced from deposited DENV-4 strain having ATCC accession number VR-2651. In some embodiments, the one or more inactivated non-dengue flaviviruses are selected from the group consisting of yellow fever group viruses and Japanese encephalitis group viruses. In some embodiments, the one or more inactivated non-dengue flaviviruses are selected from the group consisting of yellow fever virus (YFV), Japanese encephalitis virus (JEV), and West Nile virus (WNV). In some embodiments, the one or more inactivated non-dengue flaviviruses are yellow fever virus (YFV) and Japanese encephalitis virus (JEV). In some embodiments, the one or more inactivated non-dengue flavivirus includes Zika virus (ZIKV). In some embodiments, the one or more inactivated non-dengue flavivirus is Zika virus (ZIKV). In some embodiments, the one or more inactivated dengue viruses are present in an immunologically effective amount and/or the one or more inactivated non-dengue flaviviruses are present in an immunologically effective amount. In some embodiments, each of the one or more inactivated dengue viruses are present in an immunologically effective amount. In some embodiments, the one or more inactivated dengue viruses are purified and/or the one or more inactivated non-dengue flaviviruses are purified. In some embodiments, the immunogenic composition further comprises an adjuvant. In some embodiments, the immunogenic composition is a mixture of one or more inactivated DENV and XRX-001 Yellow Fever 17D inactivated vaccine (GE Healthcare). In some embodiments, the immunogenic composition is a mixture of one or more inactivated DENV and IXIARO® vaccine (Intercell USA, Inc.). In some embodiments, the immunogenic composition is a mixture of one or more inactivated DENV, XRX-001 Yellow Fever 17D inactivated vaccine (GE Healthcare), and IXIARO® vaccine (Intercell USA, Inc.).

Both the foregoing general description and the following detailed description are exemplary and explanatory only and are intended to provide further explanation of the invention as claimed. The accompanying drawings are included to provide a further understanding of the invention and are incorporated in and constitute part of this specification, illustrate several embodiments of the invention, and together with the description serve to explain the principles of the invention.

DETAILED DESCRIPTION OF THE INVENTION

The present invention relates to immunogenic compositions which comprise at least one inactivated dengue virus and at least one inactivated non-dengue flavivirus, and methods of making and using thereof. As used herein, such immunogenic compositions are referred to as "DENV+FV compositions".

A "flavivirus" refers to a virus species belonging to the genus Flavivirus in the family Flaviviridae. Flaviviruses can be grouped as set forth in the following Table 1:

TABLE 1

Tick-borne viruses

Mammalian tick-borne virus group
- Absettarov virus
- Alkhurma virus (ALKV)
- Deer tick virus (DT)
- Gadgets Gully virus (GGYV)
- Kadam virus (KADV)
- Karshi virus
- Kyasanur Forest disease virus (KFDV)
- Langat virus (LGTV)
- Louping ill virus (LIV)
- Mogiana tick virus (MGTV)
- Ngoye virus (NGOV)
- Omsk hemorrhagic fever virus (OHFV)
- Powassan virus (POWV)
- Royal Farm virus (RFV)
- Sokuluk virus (SOKV)
- Tick-borne encephalitis virus (TBEV)
- Turkish sheep encephalitis virus (TSE)

Seabird tick-borne virus group
- Kama virus (KAMV)
- Meaban virus (MEAV)
- Saumarez Reef virus (SREV)
- Tyuleniy virus (TYUV)

Mosquito-borne viruses

Without known vertebrate host
- Aedes flavivirus
- Barkedji virus
- Calbertado virus
- Cell fusing agent virus
- Chaoyang virus
- Culex flavivirus
- Culex theileri flavivirus
- Culiseta flavivirus
- Donggang virus
- Hanko virus
- Ilomantsi virus
- Kamiti River virus
- Lammi virus
- Marisma mosquito virus
- Nakiwogo virus
- Nounane virus
- Nhumirim virus
- Nienokoue virus
- Palm Creek virus (PCV)
- Spanish Culex flavivirus
- Spanish Ochlerotatus flavivirus
- Quang Binh virus Aroa virus group
- Aroa virus (AROAV)
- Bussuquara virus (BSQV)
- Iguape virus (IGUV)

Dengue virus group
- Dengue virus (DENV)
- Kedougou virus (KEDV)

Japanese encephalitis virus group
- Bussuquara virus
- Cacipacore virus (CPCV)
- Koutango virus (KOUV)
- Ilheus virus (ILHV)
- Japanese encephalitis virus (JEV)
- Murray Valley encephalitis virus (MVEV)
    - Alfuy virus
- Rocio virus (ROCV)
- St. Louis encephalitis virus (SLEV)
- Usutu virus (USUV)
- West Nile virus (WNV)
- Yaounde virus (YAOV)

Kokobera virus group
- Kokobera virus (KOKV)
- New Mapoon virus (NMV)
- Stratford virus (STRV)

Ntaya virus group
- Bagaza virus (BAGV)
- Baiyangdian virus (BYDV)
- Duck egg drop syndrome virus (BYDV)
- Ilheus virus (ILHV)
- Jiangsu virus (JSV)

TABLE 1-continued

- Israel turkey meningoencephalomyelitis virus (ITV)
- Ntaya virus (NTAV)
- Tembusu virus (TMUV)

Spondweni virus group
- Spondweni virus (SPOV)
- Zika virus (ZIKV)

Yellow fever virus group
- Banzi virus (BANV)
- Bamaga virus (BGV)
- Bouboui virus (BOUV)
- Edge Hill virus (EHV)
- Jugra virus (JUGV)
- Saboya virus (SABV)
- Sepik virus (SEPV)
- Uganda S virus (UGSV)
- Wesselsbron virus (WESSV)
- Yellow fever virus (YFV)

Viruses with no known arthropod vector

- Tamana bat virus (TABV)

Entebbe virus group
- Entebbe bat virus (ENTV)
    - Sokoluk virus
- Yokose virus (YOKV)

Modoc virus group
- Apoi virus (APOIV)
- Cowbone Ridge virus (CRV)
- Jutiapa virus (JUTV)
- Modoc virus (MODV)
- Sal Vieja virus (SVV)
- San Perlita virus (SPV)

Rio Bravo virus group
- Bukalasa bat virus (BBV)
- Carey Island virus (CIV)
- Dakar bat virus (DBV)
- Montana myotis leukoencephalitis virus (MMLV)
- Phnom Penh bat virus (PPBV)
- Rio Bravo virus (RBV)

Non vertebrate viruses

- Soybean cyst nematode virus 5

Viruses known only from sequencing

- Aedes flavivirus
- Aedes cinereus flavivirus
- Aedes vexans flavivirus
- Culex theileri flavivirus A dengue virus (DENV) is a species of the genus Flavivirus. There are 4 serotypes of dengue virus. As used herein, a DENV of serotype 1 is referred to as "DENV-1", a DENV of serotype 2 is referred to as "DENV-2", a DENV of serotype 3 is referred to as "DENV-3", and a DENV of serotype 4 is referred to as "DENV-4". As used herein, a "non-dengue flavivirus" refers to a flavivirus other than one belonging to the dengue virus group as set forth in Table 1. Vaccination with a tetravalent inactivated dengue virus vaccine composed of a mixture of inactivated DENV-1, inactivated DENV-2, inactivated DENV-3, and inactivated DENV-4 results in protective immunity against all 4 serotypes. See Fernandez, et al. (2015) Am J Trop Med Hyg 92(4):698-708, which is herein incorporated by reference in its entirety.

Prior to the present invention, however, it was unknown whether vaccination with two or more different species of flavivirus would result in immunologic interference since different species of other genuses, such as alphaviruses, result in immunologic interference, and in view of conflicting evidence of immunologic interference with the 17D vaccine with prior infections by flaviviruses such as JEV. See e.g., McClain, et al. (1998) J Infect Dis 177:634-641; Thomas, et al. (2011) Curr Opin Infect Dis 24:442-450; and VACCINES, 6th Ed. Plotkin, et al. Elsevier Health Sciences, 2012, pp. 931-932. In other words, prior to the present invention, it was unknown whether vaccinating a subject with a composition comprising an inactivated dengue virus and an inactivated non-dengue flavivirus would result in immunologic interference, thereby preventing or reducing the protective efficacy against the dengue virus and/or the non-dengue flavivirus as compared to the protective efficacy conferred by vaccinating with only a single species of flavivirus. As disclosed herein, it was found that DENV+FV compositions, i.e., comprising a mixture of at least one inactivated dengue virus and at least one inactivated non-dengue flavivirus, provides a protective immune response without immunologic interference when administered to subjects.

Therefore, the present invention provides immunogenic compositions comprising, consisting essentially of, or consisting of one or more inactivated dengue virus (DENV) and one or more inactivated non-dengue flavivirus (FV). In some embodiments, the immunogenic compositions of the present invention result in an immune response without immunologic interference between the one or more inactivated DENV and the one or more inactivated FV when administered to a subject. In some embodiments, the immunogenic compositions according to the present invention comprise, consist essentially of, or consist of at least one inactivated DENV and one inactivated FV. In some embodiments, the immunogenic compositions according to the present invention comprise, consist essentially of, or consist of at least one inactivated DENV and two inactivated FVs. As used herein, the use of "consisting essentially of" means that the given immunogenic composition may comprise one or more immunogenic agents (e.g., antibodies or antigens) in addition to the at least one inactivated DENV and the at least one inactivated FV so long as the immunogenic agents do not change the immunogenic efficacy of the combination of the at least one inactivated DENV and the at least one inactivated FV against the given DENV and FV (without the given immunogenic agent). As used herein, the use of "consisting of" means that the given immunogenic composition explicitly excludes additional immunogenic agents with the exception of immunogens resulting from the preparation and purification of the one or more inactivated DENV and the one or more inactivated FV, pharmaceutically acceptable carriers, adjuvants, auxiliaries, binders, buffers, colorants, diluents, dispersants, excipients, fillers, gelling agents, plasticizers, preservatives, solubilizing agents, stabilizers, solvents, surfactants, suspending agents, thickening agents, wetting agents, and the like, which are known in the pharmaceutical arts. In some embodiments, the adjuvant is alum, an aluminum salt such as aluminum hydroxide, or tocopherol such as AS03B or AS01E (GlaxoSmithKline). As used herein, "pharmaceutically acceptable carrier" is used interchangeably with "physiologically acceptable carrier" and includes any material that is non-reactive in the subject, and when combined with an active ingredient, allows the ingredient to retain biological activity.

The one or more inactivated dengue viruses and/or the one or more inactivated non-dengue flaviviruses in the DENV+FV compositions according to the present invention may be purified. As used herein, a "purified" inactivated virus means that an amount of the macromolecular components of the cells used to propagate the virus have been removed. In some embodiments, the amount removed from the one or more inactivated viruses is at least about 60%, at least about 70%, at least about 75%, at least about 80%, at least about 85%, at least about 90%, at least about 95%, at least about 96%, at least about 96%, at least about 97%, at least about 98%, at least about 99%, or 100% of the macromolecular components. In some embodiments, the DENV+FV compositions according to the present invention are free of at least about 60%, at least about 70%, at least about 75%, at least about 80%, at least about 85%, at least about 90%, at least about 95%, at least about 96%, at least about 96%, at least about 97%, at least about 98%, at least about 99%, or 100% of the macromolecular components.

In some embodiments, the DENV+FV compositions according to the present invention may be administered to subjects to induce the production of antibodies against the dengue virus(es) and the non-dengue flavivirus(es) in the given DENV+FV composition. Administration of the DENV+FV compositions according to the present invention may be carried out by any suitable means, including parenteral injection (such as intraperitoneal, subcutaneous, or intramuscular injection), using methods known in the art. A DENV+FV composition according to the present invention may be administered to a subject who is susceptible to or otherwise at risk of infection by or exposure to the dengue virus(es) and/or the non-dengue flavivirus(es) in the given DENV+FV composition in an immunogenically effective amount. As used herein, an "immunogenically effective amount" refers to an amount that induces an immune response, e.g., antibodies (humoral) against the dengue virus(es) and the non-dengue flavivirus(es) in the given DENV+FV composition, when administered to a subject. The immunogen(s) in the compositions may also induce cellular (non-humoral) immune responses. Such immunogenically effective amounts can be readily determined using methods known in the art and depend on the subject's state of health and weight, the mode of administration, the nature of the formulation, etc. The amount of each inactivated virus in DENV+FV compositions according to the present invention may be adjusted, e.g., increased or decreased, to result in a formulation comprising immunologically effective amounts of each. The amounts of each inactivated virus in a given DENV+FV composition may be the same or different.

Single or multiple administration of the DENV+FV compositions according to the present invention may be carried out. Multiple administration may be required to elicit sufficient levels of immunity. Levels of induced immunity can be monitored by measuring amount of neutralizing secretory and serum antibodies, and dosages adjusted or vaccinations repeated as necessary to maintain desired levels of protection.

The following examples are intended to illustrate but not to limit the invention.

Tetravalent Purified Inactivated Dengue Vaccine

A tetravalent purified inactivated dengue vaccine (TDENV-PIV) was developed at the Walter Reed Army Institute of Research (WRAIR) based on DENV-1 (WP-74), DENV-2 (S16803), DENV-3 (CH53489), and DENV-4 (TVP-360) virus strains, which were adapted to Vero cells suitable for vaccine manufacture to produce Master and Production seeds. These dengue virus strains are also identified by ATCC designators VR-2649, VR-2650, VR-2654, and VR-2651, respectively. See U.S. Pat. No. 6,190,859, which is herein incorporated by reference in its entirety. Each DENV strain was used to make a monovalent purified inactivated vaccine using methods known in the art and then combined as a mixture to give the tetravalent purified inactivated dengue vaccine. See e.g., U.S. Pat. No. 6,254,873; Putnak, et al. (1996) J Infect Dis 174:1176-84; and Putnak, et al. (1996) Am J Trop Med Hyg 55:504-10, which are herein incorporated by reference in their entirety. Other purified inactivated dengue compositions comprising, for example, one DENV serotype, all 4 DENV serotypes, or any combination of 2-3 DENV serotypes may be prepared and used according to the present invention. As used herein, "DENV1-4" refers to a mixture of inactivated dengue viruses comprising all 4 serotypes.

Purified Inactivated Yellow Fever Vaccine

The yellow fever virus (YFV) is a flavivirus species that belongs to the yellow fever virus group as set forth in Table 1.

Two inactivated yellow fever virus vaccines are 17DD and XRX-001. The 17DD vaccine is based on the YFV 17DD strain cultivated in Vero cells, inactivated with β-propiolactone, and adsorbed to aluminum hydroxide. See Pereira, et al. (2015) Vaccine 33(35):4261-4268, which is herein incorporated by reference in its entirety. The XRX-001 vaccine is based on the YFV 17D strain cultivated in Vero cells, inactivated with beta-propiolactone (BPL), and formulated with aluminum hydroxide. See Monath, et al. (2010) Vaccine 28(22):3827-3840; and Monath, et al. (2011) N Engl J Med 364:1326-1333, which are herein incorporated by reference in their entirety.

Purified Inactivated Japanese Encephalitis Virus Vaccine

Japanese encephalitis virus (JEV) is closely related to the West Nile virus (WNV) and the St. Louis encephalitis virus, which all belong in the JEV sero-complex. See Tsai T R, Solomon T, D. V. Flaviviruses (yellow fever, dengue, dengue hemorrhagic fever, Japanese encephalitis, West Nile, St. Louis encephalitis, tick-borne encephalitis). In: Mandell G L, Bennett J E, R. D, eds. Principals and practice of infectious diseases. 6th ed. Philadelphia: Elsevier; 2004: 1926-1950, which is herein incorporated by reference.

The IXIARO® vaccine (Intercell USA, Inc., a subsidiary of Valneva Austria GmbH) is based on the JE SA14-14-2 virus strain propagated in Vero cells, concentrated, purified, inactivated with formalin, and formulated with aluminum hydroxide.

Production of Inactivated Virus Vaccines

For production of each inactivated virus for incorporation into the DENV+FV compositions exemplified in the experiments herein, banked Vero cells certified for vaccine production were seeded into four to five 850 cm$^2$ roller bottles, fed with Eagle's Minimal Essential Medium (EMEM)/10% Fetal bovine serum (FBS), and incubated on a roller apparatus (1 rpm) at 35° C. until 95-100% confluent. Confluent cultures were infected with virus in 10 ml of EMEM at a multiplicity of infection (moi) of approximately 0.01 plaque-forming units (pfu) per cell, incubated at 35° C., at 1 rpm, then re-fed with 200 ml of EMEM/2% FBS. At day 3 post-infection (only trace of cytopathic effect evident) the cultures were washed 3× with serum free EMEM, 200 ml per wash, then re-fed with 200 ml serum free EMEM. Culture supernatant fluids were harvested on day 5, 7, 9, and 11 post-infection, followed by re-feeding of the cultures with serum-free EMEM.

The harvested supernatants were clarified by filtration through a 0.45 µm filter unit to remove any whole cells or cell debris and then stored at 4° C. the collected harvests (4-5 L) were pooled and concentrated approximately 80- to 100-fold by tangential flow ultrafiltration using a Filtron brand Omega 100K Screen Channel membrane ultrafilter cassette. The virus concentrate was treated with 2 mg/ml of protamine sulfate, incubated at 4° C., 2 hours, and centrifuged at 13,000 rpm, 5 minutes, 4° C., in a TY30 rotor to precipitate residual nucleic acids and some contaminating cellular proteins. The pooled virus supernatant were applied to 15-60% (w/w) sucrose gradients and centrifuged at 17,000 rpm, 18 hours, 4° C., in a Beckman SW28 rotor. The visible viral bands were collected in one ml fractions from the bottom of the tubes using a mineral oil displacement fraction collector. The virus peak was located by testing 10 µl of each fraction in a virus hemagglutination (HA) assay with goose red blood cells, and the fraction with the peak HA titer and fractions with at least one quarter of the peak HA titer were pooled.

Protein assay (Biorad) was performed on the virus pool to determine the appropriate dilution factor prior to inactivation. Virus inactivation was carried out in the presence of 1:2000 (5 mM) formalin at 22° C. for 10 days with filtration through a 0.22 µm filter and transfer to a fresh container at 48 hours. At day 10, sodium bisulfite was added in equimolar amounts to neutralize the residual formalin and the composition comprising the inactivated virus was filtered using a 0.22 µm filter and stored in bulk at 4° C. protected from light. Alternatively, diafiltration was used to remove residual formalin. The bulk compositions were assayed for sterility, protein, and antigen content using established standard operating procedures. Residual infectivity was assayed by inoculation of 5% of the lot volume onto Vero cell cultures and incubation for 14 days, sufficient to amplify any remaining infectious virus, which can then be detected by plaque assay on Vero cells. Following inactivation, the bulk compositions were mixed with aluminum hydroxide (an adjuvant designed to improve immunogenic potency) or other adjuvant, as appropriate, at the time of formulation as a DENV+FV composition. The DENV+FV compositions were formulated to contain 2.5 micrograms (µg) of each virus antigen based on previous monkey studies with alum-adjuvanted, inactivated DENV and JEV vaccines. See e.g., Fernandez, et al. (2015) Am J Trop Med Hyg 92(4):698-708, which is herein incorporated by reference in its entirety.

Prior to formulation into a DENV+FV composition, each bulk composition may be formulated with a given adjuvant (which may be the same or different) and then adjuvanted bulk compositions may be used to formulate a DENV+FV composition. Alternatively, the bulk compositions may be mixed together first and then one or more adjuvants may be added to the mixture.

Attenuated and inactivated flavivirus vaccines, such as the 17DD, XRX-001, and IXIARO® vaccines, may be obtained and used to make DENV+FV compositions according to the present invention. If an attenuated flavivirus vaccine is used, it may be inactivated using methods known in the art.

Vaccine Potency Testing

Immunogenic potency testing was performed by administering the individual monovalent vaccines or polyvalent vaccine combinations (DENV1-4, and DENV+FV compositions) by intramuscular injection to 5-6 week-old, female, Swiss-ICR mice, group sizes of 10, in four- to five-fold serially graded doses from one nanogram to one microgram per 0.1 ml dose, as required to reach an endpoint. An immunogenicity control group (N=10) received saline instead of vaccine. The mice were boosted on day 28 and bled on day 42. Sera were tested by micro-neutralization (MN) assay to determine seroconversion rates and virus neutralizing antibody titers for each virus. The median immunizing dose ($ID_{50}$) was calculated by probit. Vaccine potency may be monitored by periodic testing throughout the study.

Non-Human Primate Studies

Compositions comprising purified inactivated dengue viruses of serotypes DENV-1, DENV-2, DENV-3, and DENV-4 (DENV1-4) combined with either purified inactivated YFV 17D (DENV1-4+YFV) or purified inactivated JEV SA14-14-2 (DENV1-4+JEV) were used to vaccinate rhesus macaques to exemplify the immunogenic efficacy of DENV+FV compositions according to the present invention. Rhesus macaques are accepted animal models for demonstrating the immunogenicity and protective efficacy of flavivirus vaccines. Twenty (20) healthy adult rhesus macaques, Indian strain, both males or females, at least 4 kg in weight, flavivirus naïve including negative for antibodies to DENV serotypes 1-4, JEV, YFV, West Nile (WNV), and St. Louis Encephalitis (SLEV) viruses were used for this study. The animals were randomly assigned to groups (N=5 animal per group), vaccinated, boosted, and sera collected during the course of the study tested for virus neutralizing antibodies against DENV serotypes 1-4, YFV, and JEV. The results are set forth in Table 2. As shown in Table 2, DENV+FV compositions according to the present invention are immunogenic, elicit virus type specific neutralizing antibodies against DENV and against the given non-dengue flavivirus, which increased 10-fold or more after the second dose. Specifically, the DENV1-4+YFV and the DENV1-4+JEV compositions resulted in neutralizing antibodies against each virus present in the given composition with no evidence of immunologic interference among different viral antigens. In particular, the results show that compositions comprising inactivated dengue viruses and inactivated non-dengue flaviviruses (DENV+FV compositions) do not result in immunologic interference when administered to subjects.

should also be naïve to WNV and SLEV) as demonstrated by negative PRNT and/or HAI assays. Preferably, the macaques are also simian retrovirus (STLV, SIV) negative.

The animals are randomly allocated (e.g., by block randomization using nQuery Advisor) to receive the test compositions, i.e., the given DENV+FV composition and controls (e.g., vehicle, a composition comprising only the inactivated DENV present in the given DENV+FV composition, and/or a composition comprising only the inactivated non-dengue flavivirus(es) present in the given DENV+FV composition. Prior to all out-of-cage procedures the animals may be anesthetized with Ketamine/Acepromazine administered intramuscularly. The test compositions are administered intramuscularly in a suitable large muscle (e.g., deltoid) according to a given schedule such as that provided in Table 3.

Following vaccinations, the animals are observed for local side effects (e.g., redness, swelling) and systemic side effects (e.g., lethargy, loss of appetite). Conventional IgM and IgG ELISA performed on sera collected 7 to 14 days after immunization may be used to discriminate between primary and secondary-type immune responses in the animals. Virus neutralizing antibodies in sera is measured by virus plaque reduction neutralization test (PRNT) or microneutralization (MN) assay for DENV (all 4 serotypes) and the given non-dengue flavivirus(es) at selected time

TABLE 2

Immune Responses of *Rhesus Macaques* Vaccinated with a DENV + FV Composition

| Vaccine Groups | Immunizations[1] | Group geometric mean virus neutralizing antibody titers vs. | | | | | |
|---|---|---|---|---|---|---|---|
| | | JEV | YFV | DENV-1 | DENV-2 | DENV-3 | DENV-4 |
| DENV1-4 alone[2] | Pre-vaccination | <10 | <10 | <10 | <10 | <10 | <10 |
| | Post dose-1 | <10 | <10 | 83 | 121 | 114 | 55 |
| | Post dose-2 | <10 | <10 | 712 | 2255 | 1610 | 2295 |
| DENV1-4 + YFV[3] | Pre-vaccination | <10 | <10 | <10 | <10 | <10 | <10 |
| | Post dose-1 | <10 | 252 | 71 | 89 | 44 | 42 |
| | Post dose-2 | <10 | 1507 | 735 | 968 | 1318 | 1309 |
| DENV1-4 + JEV[4] | Pre-vaccination | <10 | <10 | <10 | <10 | <10 | <10 |
| | Post dose-1 | 20 | <10 | 29 | 38 | 61 | 49 |
| | Post dose-2 | 771 | <10 | 473 | 1097 | 882 | 934 |
| Placebo[5] | Pre-vaccination | <10 | <10 | <10 | <10 | <10 | <10 |
| | Post dose-1 | <10 | <10 | <10 | <10 | <10 | <10 |
| | Post dose-2 | <10 | <10 | <10 | <10 | <10 | <10 |

[1]Animals (5 per group) were immunized intramuscularly on days 0 and 28 with 0.5 ml of the indicated vaccine or with a placebo (negative control). Each vaccine contained 2.5 µg of each indicated virus type adsorbed to 0.5% aluminum hydroxide. Blood samples collected on days 0, 28, and 60 were tested for virus neutralizing antibodies by Microneutralization (MN) ELISA, with a cut-off of 1:10 (antibody negatives are <10).
[2]DEN V1-4 = Composition comprising purified inactivated dengue viruses of serotypes 1 to 4 (DENV-1, DENV-2, DENV-3, and DENV-4) in a pharmaceutically acceptable carrier.
[3]DENV1-4 + YFV = Composition comprising purified inactivated dengue viruses of serotypes 1 to 4 (DENV-1, DENV-2, DENV-3, and DENV-4) and purified inactivated YFV 17D in a pharmaceutically acceptable carrier.
[4]DENV1-4 + JEV = Composition comprising purified inactivated dengue viruses of serotypes 1 to 4 (DENV-1, DENV-2, DENV-3, and DENV-4) and purified inactivated JEV SA14-14-2 in a pharmaceutically acceptable carrier.
[5]Phosphate-buffered saline (PBS) control Additional Non-Human Primate Vaccine Studies Additional non-human primate vaccine studies using DENV+FV compositions containing one or more inactivated DENV (including any combination of 1-4 DENV serotypes) combined with one or more inactivated non-dengue flaviviruses selected from the Tick-borne viruses and Mosquito-borne viruses, such as YFV, JEV, WNV, SLEV, ZIKV, and combinations such as YFV+JEV, may be conducted as follows.

Healthy adult rhesus macaques, Chinese or Indian strain, male or female, at least 4 kg in weight, flavivirus naïve to DENV (serotypes 1-4) and also to the given inactivated non-dengue flavivirus and viruses closely related to the given inactivated non-dengue flavivirus (e.g., if the inactivated non-dengue flavivirus is JEV, then the macaques points. Neutralizing antibodies directed against serotype-specific epitopes in domain 3 of the virus envelope (E) protein (EDIII) may be measured by a competitive Luminex® assay (described below) for the four DENVs, and also for the given non-dengue flavivirus(es). A competitive antibody-capture ELISA may be performed using antigens prepared from virus infected cell culture supernatants. At a given time after vaccination, the animals are challenged with live dengue virus and/or a live form of the given non-dengue flavivirus(es) by subcutaneous inoculation. Blood is collected at given intervals for measuring the animals' immune responses to vaccination and viremia (as an infection marker) after virus challenge. If the non-dengue flavivirus is JEV, since there is no BSL-2 JE challenge virus strain available that is capable of inducing viremia, anti-JEV neutralizing antibody titers of 1:10 or greater following vaccination may be used as a protection correlate.

TABLE 3

| Study Day | Event | Blood Collection Volume (total) |
|---|---|---|
| −14 | Pre-study screening (PRNT, HAI) | 5 ml (5 ml) |
| 0 | Study baseline (for antibody assays) Vaccine dose 1 | 5 ml (10 ml) |
| 14 | Antibody measurements | 5 ml (15 ml) |
| 28 | Antibody measurements Vaccine dose 2 | 5 ml (20 ml) |
| 35 | Antibody measurements | 5 ml (25 ml) |
| 42 | Antibody measurements | 5 ml (30 ml) |
| 60 | Antibody measurements (groups 1, 3, and 4 go off-protocol) | 5 ml (35 ml) |
| 150 | Antibody measurement. Virus Challenge | 5 ml (40 ml) |
| 151-164 | Viremic phase blood collections | 2 ml per animal per day for 14 consecutive days (68 ml) |
| 180 | Final bleed for antibody to virus challenge | 5 ml (73 ml) |

A. Production of vaccine and control formulations: Vero cells qualified for vaccine production are seeded into four to five 850 cm² roller bottles, fed with EMEM/10% FBS, and incubated on a roller apparatus (1 rpm) at 35° C. until 95-100% confluent. Confluent cultures are infected with virus in 10 ml of EMEM at a multiplicity of infection (moi) of approximately 0.01 plaque-forming units (pfu) per cell, incubated at 35° C., at 1 rpm, then re-fed with 200 ml of EMEM/2% FBS. At day 3 post-infection (or when there is just a trace of cytopathic effect evident) the cultures are washed 3× with serum free EMEM, 200 ml per wash, then re-fed with 200 ml serum free EMEM. Culture supernatant fluids are harvested on day 5, 7, 9, and 11 post-infection, followed by re-feeding of the cultures with serum free EMEM. The harvested supernatants are clarified by filtration through a 0.45 μm filter unit to remove any whole cells or cell debris and then stored at 4° C. The collected harvests (4-5 L) are pooled and concentrated approximately 80- to 100-fold by tangential flow ultrafiltration using a Filtron brand Omega 100K Screen Channel membrane ultrafilter cassette. The virus concentrate are treated with 2 mg/ml of protamine sulfate, incubated at 4° C., 2 hours, and centrifuged at 13,000 rpm, 5 minutes, 4° C., in a TY30 rotor to precipitate residual nucleic acids and some contaminating cellular proteins. The pooled virus supernatant will then be applied to 15-60% (w/w) sucrose gradients and centrifuged at 17,000 rpm, 18 hours, 4° C., in an SW28 rotor. The visible viral bands are collected in one ml fractions from the bottom of the tubes using a mineral oil displacement fraction collector. The virus peak are located by testing 10 μl of each fraction in an HA assay with goose red blood cells, and the fraction with the peak HA titer and fractions at least one quarter of the peak titer are pooled. Protein assay (Biorad micro BCA) are performed on the virus pool to determine the appropriate dilution factor prior to inactivation. Virus inactivation are carried in the presence of a 1:2000 dilution of formalin (5 mM) at 22° C. for 10 days with filtration through a 0.22 μm filter and transfer to a fresh container at 48 hours. At day 10, the compositions are diafiltered to remove residual formalin and then sterile filtered through a 0.22 μm filter and stored in bulk at 4° C. protected from light. The bulk compositions are assayed for sterility, protein content, and antigen content using established SOPs. Residual viral infectivity are tested by inoculation of 5% of the vaccine lot volume onto Vero cell cultures and incubation for 14 days, sufficient to amplify any remaining infectious virus, which will then detected by plaque assay on Vero cells.

Prior to testing in rhesus macaques, the vaccines are tested for immunogenicity in mice, e.g., at Harlan Biosciences (Harlan Protocol 421-09. Rodent Immunization for Antibody Production. IACUC approval November 2012), and then formulated to a desired dosage with a given adjuvant such as aluminum hydroxide (0.1 to 0.5%). For example, potency testing may be performed by administering the vaccines by IM injection to 5-6 week-old, female, Swiss-ICR mice, in four- to five-fold serially graded doses from one nanogram to one microgram per 0.1 ml dose, as required to reach a given endpoint. An immunogenicity control group is administered saline instead of vaccine. The mice are boosted on day 28, exsanguinated on day 42, and the blood processed to sera. The sera is aliquoted and frozen at −20° C. The mouse sera is assayed by PRNT to determine seroconversion rates (50% or greater plaque reduction at the 1:10 assay cut-off) and virus neutralizing antibody titers for each virus. The median (50%) immunizing dose ($ID_{50}$) will be calculated by probit analysis (SPSS). Vaccine potency may be monitored by periodic testing throughout the study.

B. Viruses. Viruses used in the serological assays may be low-passage level, e.g., Vero cell adapted stocks of DENV-1 (WP 74), DENV-2 (S16803), DENV-3 (CH53489), DENV-4 (341750 or TVP-360), inactivated JEV SA14-14-2, attenuated YFV 17D inactivated YFV 17D, and an attenuated WN replicon (for laboratory PRNT assays).

C. Plaque reduction neutralization test (PRNT). Test sera are diluted in EMEM with 2% heat-inactivated FBS serially, four-fold, from 1:10 to 1:640 or greater depending on the titer. An equal volume of each flavivirus present in the given DENV+FV composition adjusted to an infectivity concentration of 500 PFU/ml are added to each serum serial dilution tube and incubated at 35° C. for 30 minutes. After incubation, 0.2 ml of each serum-virus mixture are inoculated to six-well plates (in triplicate wells) containing confluent monolayers of Vero-81 cells (ATCC). The plates are rocked gently and incubated at 35° C. with 5% $CO_2$ for 60 minutes to allow for virus adsorption, then the cell monolayers are overlayered with 2.5 ml of a 1% nutrient agarose overlay (EMEM, 2% FCS), L-Glut, NEAA, 1% LMA Sea Plaque agarose) and incubated at 35° C. with 5% $CO_2$ for 3-5 days depending on the virus plaque size. Viral plaques are visualized by staining with neutral red (Sigma) in 1% agarose/saline and incubated at 35° C. with 5% $CO_2$ for 12-24 hours. Plaques are counted and plaque reduction 50% endpoint ($PRNT_{50}$) titers are calculated by probit analysis implemented on a PC running SPSS statistical software (SPSS Inc.).

D. Microneutralization (MN) ELISA. Serum samples are serially diluted three-fold in 96-well micro-plates for dilutions from 1:10 to 1:7,290 (if needed). One hundred microliters of a calibrated virus dose (the highest virus dilution that produces ≥1.0 ELISA $OD_{405}$ value after a five-day incubation) are added to 100 μL of each serum dilution and incubated at room temperature for 2 hours. After incubation, the contents of the plates are transferred to microplates containing confluent Vero WHO cell monolayers from which the growth medium has been decanted. Positive (virus-only) and negative (growth medium alone) controls are included in each assay. After incubation for 4-5 days, the cells are fixed with absolute ethanol:methanol (1:1) for 1 hour at −20° C., washed three times with PBS. After washing, 100 μL of 1:16,000 dilution of anti-DEN mAb 4G2

(CDC) in antibody sample diluent are added to each well and incubated at 35° C. for 2 hours, then wash 5 times with PBS. A detection antibody (HRP-conjugate) diluted 1:4,000 are added to the plates (100 µL/well) and incubated at 35° C. for 1 hour. After incubation, the plates are washed 5 times with PBS and 100 µL/well of HRP substrate (2,2'-azino-bis(3-ethylbenzthiazoline-6-sulfonic acid, Kirkegaard and Perry Laboratories) are added to each well. The plates are read ($OD_{405}$) on a microplate reader (Titertek-Ascent). For a valid assay, the average $OD_{405}$ of three non-infected control wells of each microplate must be ≤0.4; this value are used for normalization. The virus-only control wells must have an $OD_{405}$≥1.0. The normalized OD values are transformed to a four-parameter logistical model using Graph Pad Prism version 4.0 software for Windows (Graph Pad Software) to calculate 50% MN titers using a sigmoidal dose response (variable slope) formula. The virus neutralization titer is the reciprocal of the serum dilution giving 50% reduction in the absorbance readout of the assay when compared with the virus dose control without serum. For a valid 50% MN titer, the $R^2$ value for the fitted sigmoidal curve must be ≥0.80

E. Competitive Multiplexed Luminex Immunoassay. Recombinant E domain III (EDIII) proteins of each flavivirus present in the given DENV+FV composition are covalently coupled to free carboxyl groups on xMAP Multi-Analyte COOH Microspheres (spectrally discrete polystyrene beads from Luminex Corporation) using an N-hydroxysulfosuccinimide (sulfo-NHS)-enhanced carbodiimide-mediated conjugation reaction. Monoclonal Abs are directly conjugated to R-phycoerythrin (PE) via succinyl esters containing either a thiol or maleimide reactive group. Microspheres coupled to each recombinant EDIII protein are diluted to a final concentration of $8.0 \times 10^5$ microspheres/ml and 25 µl are added to each well of a black, opaque microtiter plate (Costar). A standard reference serum pool (containing anti-flavivirus neutralizing antibodies against flavivirus present in the given DENV+FV composition) and single reference sera are used to generate a standard curve. An antibody negative serum control may also be included in each assay. Following incubation the PE-tagged type-specific mAbs (mAb-PE) are added to each well of the plate in a volume of 25 µl and mixed. After incubation, all samples are transferred to a filter plate (Millipore) pre-wetted with PBS. The serum samples are washed three times with 200 µl of PBS buffer and the EDIII-microspheres are resuspended in 200 µl of PBS plus 1% BSA for analysis on a Luminex® 200™ Total System and IS 2.3 software designed for template-based data acquisition with data regression analysis. The antibody titers of test sera are obtained by measuring the ability of a test sample to inhibit mAb-PE binding to the recombinant EDIII proteins and comparing that value to that of a dilution series of the reference standard. Specifically, relative inhibition of mAb-PE binding are compared to a standard curve by using a five-parameter logistic (5PL) function in curve fitting software, and the test sample concentration are calibrated from the fitted standard curve. The standard reference sera used for the standard curve are assigned arbitrary antibody concentrations. Data, in median fluorescent intensity (HFI) units, are processed in Bio-Plex Manager 3.0 software (Bio-Rad) or using Microsoft Excel spreadsheet (Microsoft).

F. Indirect competitive Ab-Capture ELISA. Recombinant EDIII proteins are used to coat microtiter plates. Test sera and pre-titrated type-specific neutralizing mAbs labeled with biotin are added to the pre-coated wells. After an appropriate incubation, streptavidin conjugated with enzyme (e.g., HRP), are added to each well followed by an enzyme substrate for color development. The results are read on a microplate reader (Titertek-Ascent), and antibody titers determined by a comparison with a standard curve generated from serial dilutions of appropriate serum standards G. Viremia assay. Vero cells in 25 $cm^2$ (T25) flasks are infected with 0.1 ml of serum and incubated at 35° C. for 14 days (with a complete medium change at day 7) to amplify any virus that might be present. Virus are detected by plaque assay on Vero cell monolayers stained with neutral red. Direct plaque assay of virus positive sera will then be performed to obtain viremia titers (pfu/ml). Viremia are measured independently by PCR assay.

H. Specimen handling. Blood samples are processed to sera by centrifugation at 2,500×g, 10 minutes, 20° C., and sera are divided into appropriately labeled aliquot tubes and stored frozen at −80° C. prior to assay.

However, p-values presented for these analyses are considered to represent descriptive measures of strength of evidence rather than formal statistical inference. Fisher's exact test are used to compare protection rate and seroconversion rates between control and vaccine groups. Repeated measure ANOVA are used to compare antibody titers between experimental groups. All titers are log transformed to stabilize variance. Kaplan Meier Curve are used to graph the time to viremia, and are compared between experimental groups using log-rank test.

I. Vaccination. Animals are inoculated with vaccines or controls IM with a 23 to 25 gauge, ⅝-in. to 1-in. needle and a 1 cc syringe in the upper arm. Vaccinations and virus challenge are carried out using aseptic technique after first shaving and cleaning and disinfecting the site with 70% isopropyl alcohol. The volume administered are 0.5 ml. Booster vaccinations are administered in alternate arms, but otherwise identically to the primary vaccination and according to a given schedule, e.g., Table 3.

J. Virus challenge. Challenge virus doses of 4 to 5 log 10 plaque-forming units (pfu) per ml are administered by subcutaneous (SC) inoculation of 0.5 ml of virus in sterile culture medium. The inoculation site are the loose skin of the upper medial aspect of the arm with a 23 to 25 gauge, ⅝-in. to 1-in. needle and a 1 cc syringe. Prior to inoculation, the site are shaved cleaned and disinfected with 70% isopropyl alcohol. Residual challenge virus are returned to the laboratory to verify its potency by plaque titration. Daily after challenge, for a period of 14 days, 2 ml of blood are drawn for determining the titers of circulating virus (viremia). Rhesus monkeys do not show any signs of disease following subcutaneous virus challenge; measurement of viremia, which is thought to correlate with human disease, will allow for assessment of the protective efficacy of the vaccine.

Rhesus macaques were immunized with a DENV1-4+YFV composition and later challenged with DENV-2 or YFV as set forth above. The results in Table 4 evidence that DENV+FV compositions according to the present invention provides protective immunity against the dengue virus(es) and the non-dengue flaviviruses virus(es) in the given DENV+FV.

TABLE 4

Responses to Vaccination[1] and Virus Challenge in Rhesus Macaques Receiving DENV1-4 + YFV

| Vaccine formulation | | Neutralizing antibody titers on day of challenge: Mean (range) | Challenge virus | Viremia positive animals/Total animals | Days of viremia |
|---|---|---|---|---|---|
| DENV1-4 + YFV[2] | JEV | <10 | Dengue type-2 | 0/5 | 0 |
| | YFV | 893 (161-1466) | | | |
| | DENV-1 | 145 (67-263) | | | |
| | DENV-2 | 105 (43-192) | | | |
| | DENV-3 | 80 (51-174) | | | |
| | DENV-4 | 273 (86-730) | | | |
| | JEV | <10 | Yellow fever | 0/5 | 0 |
| | YFV | 721 (194-2295) | | | |
| | DENV-1 | 347 (198-621) | | | |
| | DENV-2 | 310 (163-693) | | | |
| | DENV-3 | 209 (53-304) | | | |
| | DENV-4 | 410 (234-534) | | | |
| Placebo[3] | N/A | N/A | Dengue type-2 | 5/5 | 10 |
| | N/A | N/A | Yellow fever | 1/5 | 1 |

[1]Animals (5 per group) were immunized intramuscularly on days 0 and 28 with 0.5 ml of DENV1-4 + YFV (contained 2.5 μg of each virus type adsorbed to 0.5% aluminum hydroxide) or with a placebo (negative control). Blood samples collected on days 0, 28, and 60 were tested for virus neutralizing antibodies and viremia.
[2]DENV1-4 + YFV = Composition comprising purified inactivated dengue viruses of serotypes 1 to 4 (DENV-1, DENV-2, DENV-3, and DENV-4) and purified inactivated YFV 17D in a pharmaceutically acceptable carrier.
[3]Phosphate-buffered saline (PBS) control.

Therefore, in some embodiments, the present invention is directed to methods for immunizing subjects against one or more inactivated DENV and one or more inactivated non-dengue flaviviruses by administering to the subject a DENV+FV composition.

DENV+FV Composition Studies in Humans

Healthy male and female volunteers, ages 18-45, are examined and screened by a panel of tests, including blood chemistries, hematology, prothrombin time, partial thromboplastin time, urinalysis, rapid plasma reagin antibody, and serology for hepatitis B surface antigen and antibody to HIV. Volunteers are excluded on the basis of persistent significant abnormality or positive test. Volunteers are also excluded if they had previous flavivirus immunity, which may affect responses to dengue vaccines or a history of allergy to neomycin, streptomycin, or gentamycin. Prior flavivirus immunity is defined as having no detectable hemagglutination inhibition antibodies (at a 1:10 serum dilution) against DENV (all 4 serotypes), JEV, or YFV, and no history of being vaccinated with a flavivirus or a prior flavivirus infection.

A standard randomized, single-blind inpatient clinical protocol is used for all pilot studies. Each volunteer is vaccinated with a given dose of the given DENV+FV composition. Volunteers are monitored closely for three weeks for adverse symptoms. Blood may be collected from volunteers according to a given schedule, e.g., every other day and on day 31, for routinely available medical tests for hemoglobin and hematocrit, white blood cell count with differential count, platelet count, and aspartate aminotransferase (AST), alanine aminotransferase (ALT) levels, and antibody studies. Antibody tests may include ELISA, HAI, and plaque reduction neutralization tests (PRNT) performed using the same strains of flaviviruses provided in the given DENV+FV composition. Detection of anti-flavivirus IgM antibodies is performed by modification of an ELISA, where values >0.10 OD units are considered positive as previously described in the art. The HAI test is performed by the standard technique modified to microvolumes using 4-8 units of individual antigens, using serum extracted with acetone to remove inhibitors. See Clarke and Casals (1958) Am J Trop Med Hyg 7:561-573. PRNT assays are performed using methods known in the art.

A vaccine failure is defined as an unacceptable adverse clinical response or failure to develop convalescent IgM or PRNT antibodies.

Section headings are used for organizational purposes only and are not to be construed as defining or limiting the subject matter described. Unless explicitly provided otherwise, singular word forms include the plural forms. As used herein, "at least one" and "one or more" are used interchangeably. As used herein, the singular forms "a", "an", and "the" include plural referents unless the context clearly dictates otherwise. As used herein, "and/or" means "and" or "or". For example, "A and/or B" means "A, B, or both A and B" and "A, B, and/or C" means "A, B, C, or a combination thereof" and said "combination thereof" means "A and B, A and C, or B and C".

To the extent necessary to understand or complete the disclosure of the present invention, all publications, patents, and patent applications mentioned herein are expressly incorporated by reference therein to the same extent as though each were individually so incorporated.

Having thus described exemplary embodiments of the present invention, it should be noted by those skilled in the art that the within disclosures are exemplary only and that various other alternatives, adaptations, and modifications may be made within the scope of the present invention. Accordingly, the present invention is not limited to the specific embodiments as illustrated herein, but is only limited by the following claims.

What is claimed is:

1. An immunogenic composition comprising one or more inactivated dengue viruses and one or more inactivated non-dengue flaviviruses, an adjuvant, and a pharmaceutically acceptable vehicle, wherein said non-dengue flaviviruses are selected from the group consisting of yellow fever virus (YFV) group viruses, Japanese encephalitis virus (JEV) group viruses, and Zika virus (ZIKV).

2. The immunogenic composition of claim 1, wherein the one or more inactivated dengue viruses are selected from the group consisting of an inactivated DENV-1, an inactivated DENV-2, an inactivated DENV-3, and an inactivated DENV-4.

3. The immunogenic composition of claim 1, wherein the one or more inactivated dengue viruses consist of an inactivated DENV-1, an inactivated DENV-2, an inactivated DENV-3, and an inactivated DENV-4.

4. The immunogenic composition according to claim 1, wherein said dengue virus is an inactivated DENV-1 produced from deposited DENV-1 strain having ATCC accession number VR-2649.

5. The immunogenic composition according to claim 1, wherein said dengue virus is an inactivated DENV-2 produced from deposited DENV-2 strain having ATCC accession number VR-2650.

6. The immunogenic composition according to claim 1, wherein said dengue virus is an inactivated DENV-3 produced from deposited DENV-3 strain having ATCC accession number VR-2654.

7. The immunogenic composition according to claim 1, wherein said dengue virus is an inactivated DENV-4 produced from deposited DENV-4 strain having ATCC accession number VR-2651.

8. The immunogenic composition according to claim 1, wherein the one or more inactivated non-dengue flaviviruses are selected from the group consisting of yellow fever group viruses and Japanese encephalitis group viruses.

9. The immunogenic composition according to claim 1, wherein the one or more inactivated non-dengue flaviviruses are selected from the group consisting of yellow fever virus (YFV), Japanese encephalitis virus (JEV), and West Nile virus (WNV).

10. The immunogenic composition according to claim 1, wherein the one or more inactivated non-dengue flaviviruses are yellow fever virus (YFV) and Japanese encephalitis virus (JEV).

11. The immunogenic composition according to claim 1, wherein the one or more inactivated non-dengue flavivirus is Zika virus (ZIKV).

12. The immunogenic composition according to claim 1, wherein the one or more inactivated dengue viruses are present in an immunologically effective amount and/or the one or more inactivated non-dengue flaviviruses are present in an immunologically effective amount.

13. The immunogenic composition according to claim 1, wherein the one or more inactivated dengue viruses are purified and/or the one or more inactivated non-dengue flaviviruses are purified.

14. A method of producing antibodies against a dengue virus and a non-dengue flavivirus in a subject, which comprises administering to the subject the immunogenic composition according to claim 1.

15. The method according to claim 14, wherein the immunogenic composition is administered on Day 0 and on Day 28.

16. The method according to claim 14, wherein the administration is by intramuscular injection.

17. A medicament for producing antibodies against a dengue virus and a non-dengue flavivirus in a subject, which comprises the immunogenic composition according to claim 1.

18. A method of inducing an immune response in a subject, which comprises administering the immunogenic composition according to claim 1 to the subject.

19. The immunogenic composition according to claim 1, wherein the one or more inactivated dengue viruses and the one or more inactivated non-dengue flaviviruses, wherein when said one or more inactivated non-dengue flaviviruses are selected from the group consisting of yellow fever virus (YFV) group viruses and Japanese encephalitis virus (JEV) group viruses, do not result in immunologic interference when administered to a subject.

20. An immunogenic composition comprising an inactivated DENV-1, an inactivated DENV-2, an inactivated DENV-3, an inactivated DENV-4, and one or more inactivated non-dengue flaviviruses selected from the group consisting of yellow fever virus (YFV) group viruses and Japanese encephalitis virus (JEV) group viruses, an adjuvant, and a pharmaceutically acceptable vehicle, wherein the inactivated dengue viruses and the one or more inactivated non-dengue flaviviruses do not result in immunologic interference when administered to a subject.

* * * * *